United States Patent [19]
Edenbaum et al.

[11] Patent Number: 5,520,621
[45] Date of Patent: May 28, 1996

[54] WATER-PERMEABLE CASTING OR SPLINTING DEVICE AND METHOD OF MAKING SAME

[75] Inventors: Martin Edenbaum, Princeton Junction, N.J.; Gary Silvers, Tulsa, Okla.

[73] Assignee: Carapace, Inc., Broken Arrow, Okla.

[21] Appl. No.: 280,035

[22] Filed: Jul. 25, 1994

[51] Int. Cl.$^6$ .................................................. A61F 5/01
[52] U.S. Cl. ........................................... 602/8; 602/6
[58] Field of Search ............................ 602/4, 5, 6, 8, 602/21; 604/368, 369, 379

[56] References Cited

U.S. PATENT DOCUMENTS

| | | | |
|---|---|---|---|
| 4,193,395 | 3/1980 | Gruber | 128/90 |
| 4,235,228 | 11/1980 | Gaylord, Jr. et al. | 128/91 R |
| 4,411,262 | 10/1983 | von Bonin et al. | 128/90 |
| 4,442,833 | 4/1984 | Dahlen et al. | 128/90 |
| 4,454,873 | 6/1984 | Laufenberg et al. | 128/90 |
| 4,454,874 | 6/1984 | Monnier | 128/91 R |
| 4,502,479 | 3/1985 | Garwood et al. | 128/90 |
| 4,537,184 | 8/1985 | Williams, Jr. | 128/90 |
| 4,628,917 | 12/1986 | Campagna, Jr. et al. | 128/90 |
| 4,667,661 | 5/1987 | Scholz et al. | 128/90 |
| 4,770,299 | 9/1988 | Parker | 206/409 |
| 4,869,046 | 9/1989 | Parker | 53/416 |
| 4,899,738 | 2/1990 | Parker | 128/90 |
| 5,171,208 | 12/1992 | Edenbaum et al. | 602/6 |
| 5,318,504 | 6/1994 | Edenbaum et al. | 602/8 |
| 5,342,343 | 8/1994 | Kitaoka et al. | 604/378 |

*Primary Examiner*—Corrine M. Maglione
*Assistant Examiner*—Michael L. Arness
*Attorney, Agent, or Firm*—Panitch Schwarze Jacobs & Nadel

[57] ABSTRACT

Unitary casting devices are provided for making casts and splints. In one embodiment, the device includes a padding layer for contact with the patient, a non-hydrophilic, water-permeable inner protective layer juxtaposed against the padding layer, a casting layer comprising a liquid-activatable casting material placed along the inner protective layer, a liquid-impermeable, water vapor permeable first outer protective layer juxtaposed against the casting layer and a non-hydrophilic, water-permeable second outer protective layer juxtaposed against the first outer protective layer. The device also includes means for holding the layers together to form a unitary device. In other embodiments of the unitary device, the device further includes inner and outer water containment layers including a liquid-impermeable, water vapor permeable material such that the device need not be immersible, but may contain its own supply of activating liquid or have liquid introduced into the device.

21 Claims, 3 Drawing Sheets

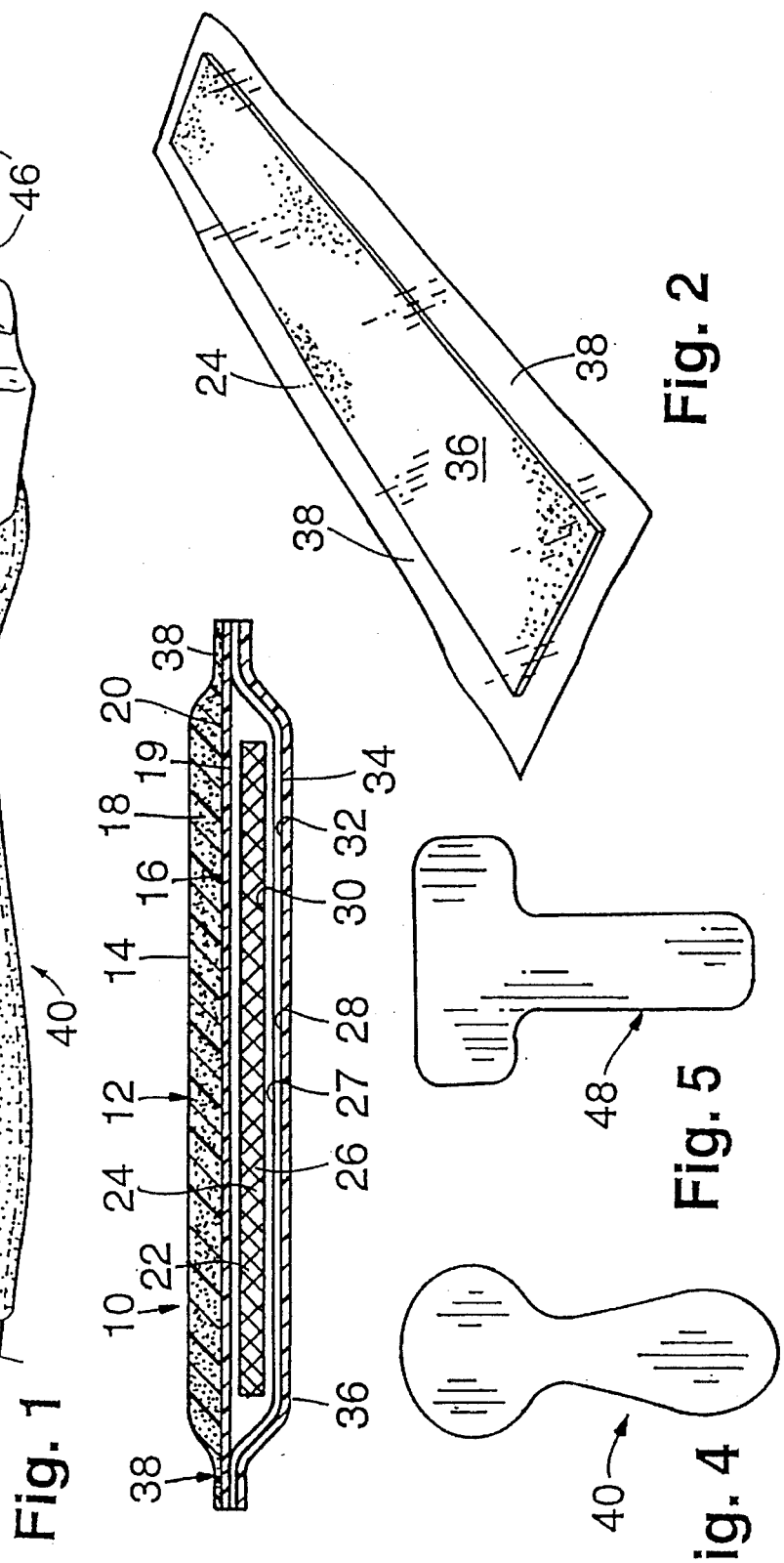
Fig. 1
Fig. 2
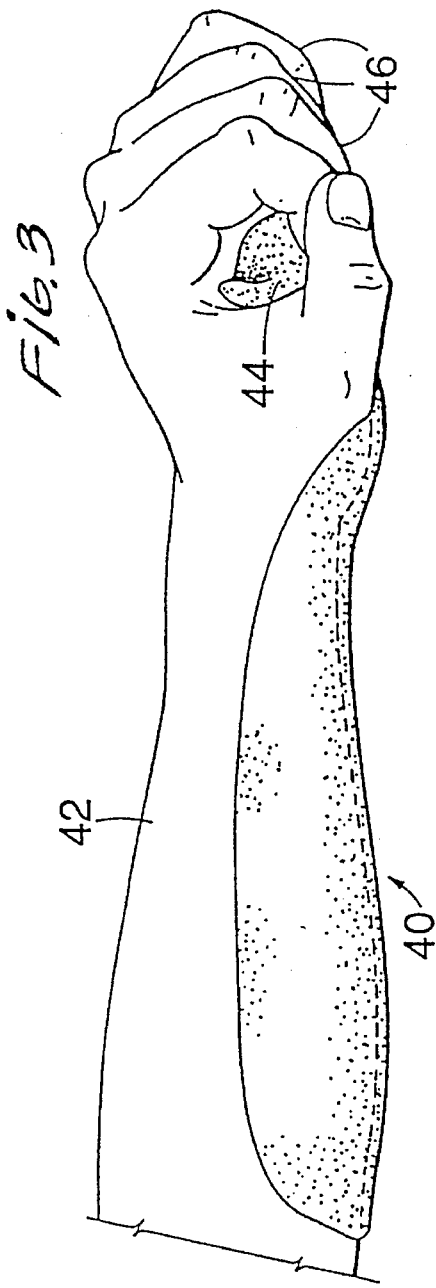
Fig. 3
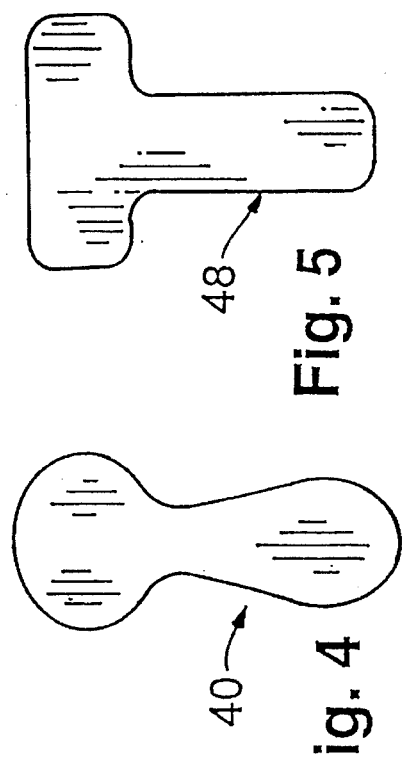
Fig. 5
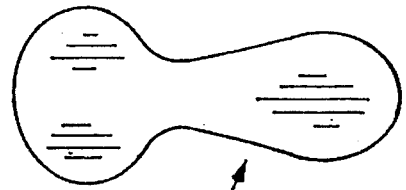
Fig. 4

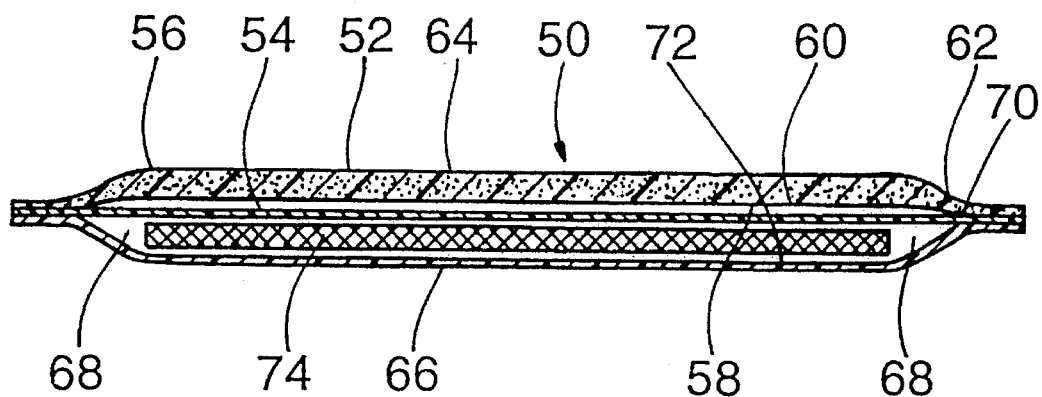
Fig. 6
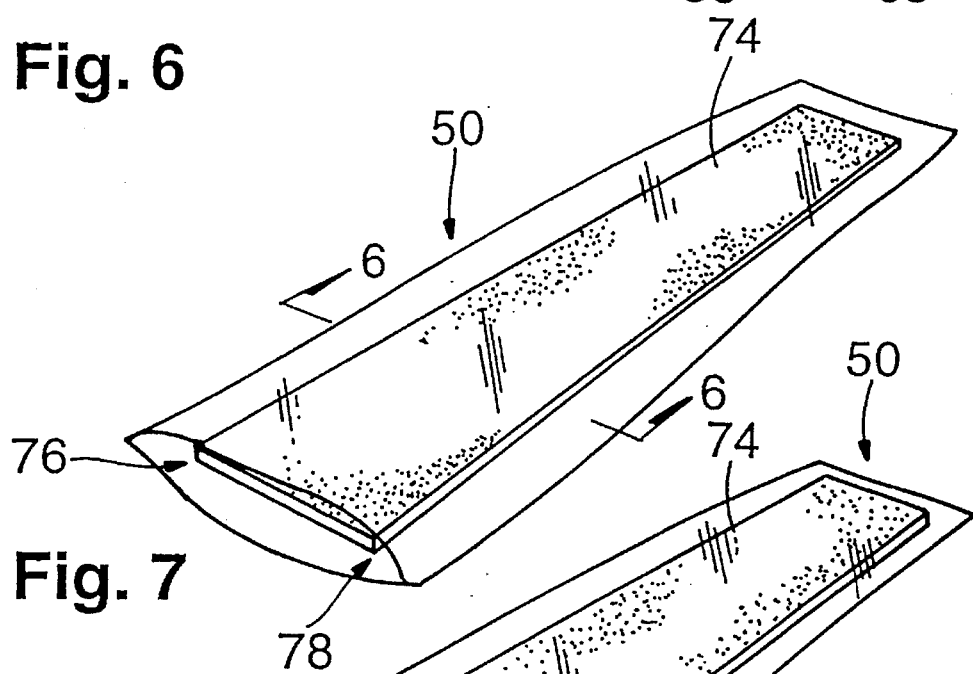
Fig. 7
Fig. 8
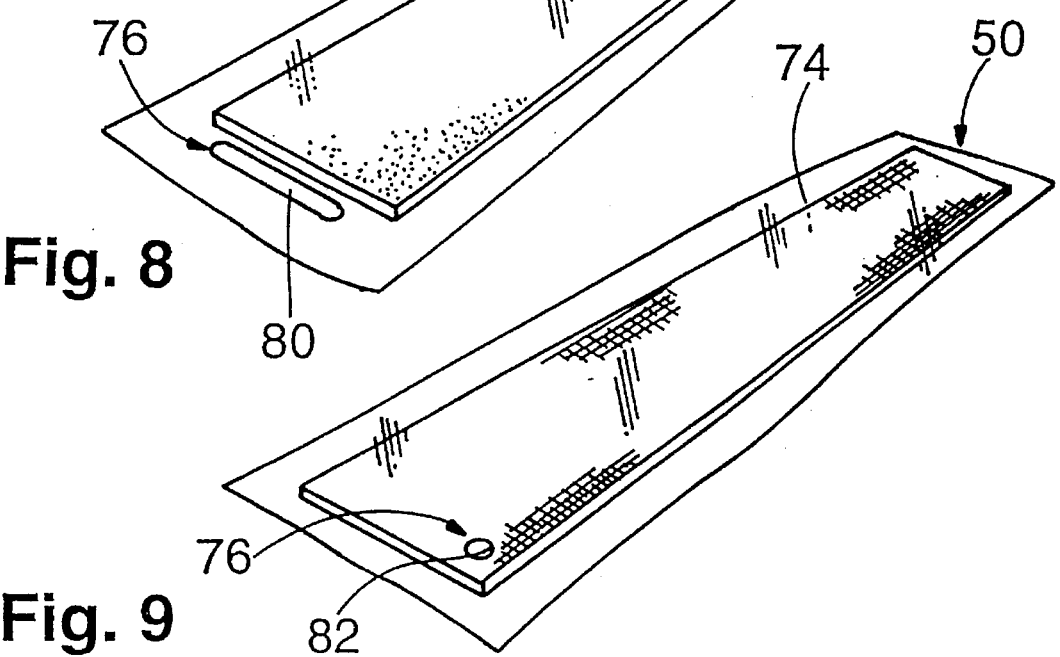
Fig. 9

WATER-PERMEABLE CASTING OR SPLINTING DEVICE AND METHOD OF MAKING SAME

FIELD OF THE INVENTION

The present invention relates to the field of medical casting and splinting devices. More particularly, it relates to a unitary preformed multilayer casting or splinting device and method of forming the same.

BACKGROUND OF THE INVENTION

Casts and splints have traditionally been made by coating or impregnating a substrate, usually fabric, such as gauze, mesh, fiberglass or the like with a dry casting material such as Plaster of Paris or various resins. The coated substrate is then dipped in water or other liquid-activating substance to initiate the "setting" of the casting material, squeezed or wrung out to express excess water, placed on the appropriate part of the patient and allowed to cure.

The process is often messy, time consuming, requires multiple supplies and considerable skill. Wet casting material can be contacted with hands, clothes, patient, floor furniture and the like. Usually the person applying the cast or splint wears gloves and protective clothing and often uses a special "casting room." If colored compounds are used, messy stains may result. If resins are used, a detackifier may be necessary. Often, a protective layer of material is placed on the patient to protect the skin (see, for example, U.S. Pat. No. 4,193,395, which refers to covering the body part with a stockinette).

Some casting devices have been described, for example in U.S. Pat. Nos. 4,235,228, 4,442,833, 4,454,874, 4,628,917, 4,770,299, 4,869,046 and 4,899,738, which enclose the casting material in sleeves or coverings of various materials so that direct contact with the casting material is not necessary.

Even those devices that enclose the casting material still require immersing the device in water, wringing and applying. This results in a wet layer of material in direct contact with the patient's skin, which may be uncomfortable and irritating and can, in time, cause maceration and sloughing of the skin. This also requires a ready source of water, which may not be available in some circumstances.

Some devices have tried placing a totally moisture impermeable layer next to the skin, for example, U.S. Pat. No. 4,454,874. This may keep moisture from the casting material from contacting the skin; however, it traps moisture that is normally released from the skin in sweating and respiration of the skin. This moisture builds up under the impermeable layer and may cause tissue damage, odor and the like. Other, non-unitary devices have used a separate dry pad or layer to be applied to the patient or adhered to the casting device after the casting device or material is wetted such as, for example, U.S. Pat. Nos. 4,193,395 and 4,628,917. These latter devices require more than one component, and adhesives usually do not hold well in a moist environment and may restrict respiration of vapor.

Other devices have been described, for example in U.S. Pat. Nos. 4,770,299, 4,869,046 and 4,899,738, which use hydrophobic material on the patient contact side, but which still require immersing the device. The immersion and "squeezing" of the device results in water being trapped or retained in the spaces of the hydrophobic material which then presents a wet surface to the patient and may trap moisture next to the patient.

The most recent unitary devices which concern the moisture retention problem of prior art casting and splinting devices are described in U.S. Pat. Nos. 5,171,208 and 5,318,504. These devices provide a layer of water-impermeable, water vapor-permeable film on the side of the device in contact with the patient's skin. The film is placed next to the patient's skin to release trapped moisture while the cast or splint is in place on the patient, thus preventing water, or other liquid from penetrating through the device to contact the patient's skin while the device is curing or if the device is exposed to liquid. Next to the water impermeable film, is a layer of water-permeable padding followed by casting material and a non-woven water permeable film of, for example, polypropylene. The devices can also be made such that they are in a condition for application without the need to fully immerse the device in liquid. In such a case, the device is made with a pre-formed liquid-containing pouch formed of water permeable spun-bonded polypropylene.

SUMMARY OF THE INVENTION

The present invention includes a unitary casting device, for making casts and splints. The device includes a padding layer which is used in contact with a patient. Juxtaposed against the padding layer is a non-hydrophilic, water-permeable inner protective layer. A casting layer, comprising a liquid-activatable casting material, is placed along the inner protective layer. A liquid-impermeable, water vapor-permeable first outer protective layer is juxtaposed against the casting layer, and a non-hydrophilic, water-permeable second outer protective layer is juxtaposed against the first outer protective layer. Means are also provided for holding the layers together to form the unitary device.

In an alternative embodiment, the unitary casting device includes a first laminated layer and a second laminated layer. The first laminated layer includes a padding layer which is used in contact with a patient and a non-hydrophilic, water-permeable inner protective layer. A casting layer, comprising a liquid-activatable casting material is placed along the inner protective layer. The second laminated layer includes a liquid impermeable, water vapor-permeable first outer protective layer, and a non-hydrophilic, water-permeable second outer protective layer. The first outer protective layer is juxtaposed against the casting layer. Means are also included for holding the laminated and casting layers together to form a unitary device.

In a further alternative embodiment, the unitary casting device includes a padding layer having a first side and a second side. The first side of the padding layer is used in contact with a patient. The first side of a non-hydrophilic, water-permeable inner protective layer is juxtaposed against the second side of the padding layer. The first side of an inner water containment layer is juxtaposed against a second side of the inner protective layer. The first side of an outer water containment layer is substantially parallel to and spaced apart from a second side of the inner water containment layer. A space is formed between the first side of the outer water containment layer and the second side of the inner water containment layer. A second side of the outer water containment layer has at least one perforation through which liquid may pass into the space. Means are included for holding the padding, the inner protective, the inner water containment and the outer water containment layers together. A casting member, formed of a liquid-activatable casting material, is positioned within the space.

The present invention also includes a method for making a unitary casting device, useful for making casts and splints. In the method, a sheet of substrate is impregnated with a dry, liquid-activatable casting material to form a casting layer having a first side and a second side. A padding layer, for use in contact with a patient, is laminated to a non-hydrophobic, water-permeable inner protective layer to form a first laminate. A liquid impermeable, water vapor-permeable first outer protective layer is laminated to a non-hydrophilic, water-permeable second outer protective layer to form a second laminate. The first side of the casting layer is covered with the first laminate such that the first side of the casting layer is juxtaposed to the inner protective layer. The second side of the casting layer is covered with the second laminate such that the second side of the casting layer is juxtaposed to the first outer protective layer. The first and second laminates are sealed together such that the casting layer is enclosed, thereby forming a unitary device.

BRIEF DESCRIPTION OF THE DRAWINGS

The foregoing summary, as well as the following detailed description of preferred embodiments of the invention, will be better understood when read in conjunction with the appended drawings. In the drawings, like numerals are used to indicate like elements throughout. For the purpose of illustrating the invention, there are shown in the drawings embodiments which are presently preferred. It should be understood, however, that the invention is not limited to the precise arrangements and instrumentalities shown. In the drawings:

FIG. 1 is a cross sectional view of an embodiment of a unitary device according to the present invention;

FIG. 2 is a perspective view of an embodiment of the unitary device shown in FIG. 1 during construction;

FIG. 3 is a side elevational view of the device of FIG. 1 as applied to the arm of a patient;

FIG. 4 is a front elevational view of a splint formed from an embodiment of a unitary device according to the present invention;

FIG. 5 is a further front elevational view of a splint formed from an embodiment of a unitary device according to the present invention;

FIG. 6 is a cross sectional elevational view of an alternative embodiment of a unitary device according to the present invention;

FIG. 7 is a perspective view of the device as shown in FIG. 6 with an open end;

FIG. 8 is a perspective view of the device as shown in FIG. 6 with a reservoir; and FIG. 9 is a perspective view of the device as shown in FIG. 6 with a portal.

DETAILED DESCRIPTION OF PREFERRED EMBODIMENTS

Figure 10:
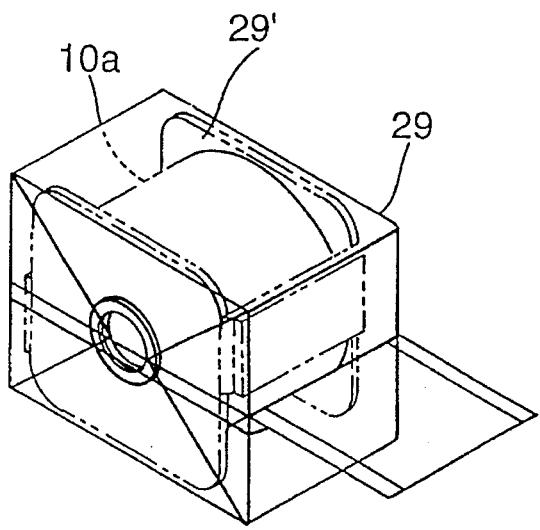
FIG. 10 is a perspective view of the device of FIG. 1 in roll form.

Certain terminology is used in the following description for convenience only and is not limiting. The words "right," "left," "lower" and "upper" designate directions in the drawings to which reference is made. The terminology includes the words above specifically mentioned, derivatives thereof, and words of similar import.

Figure 11:
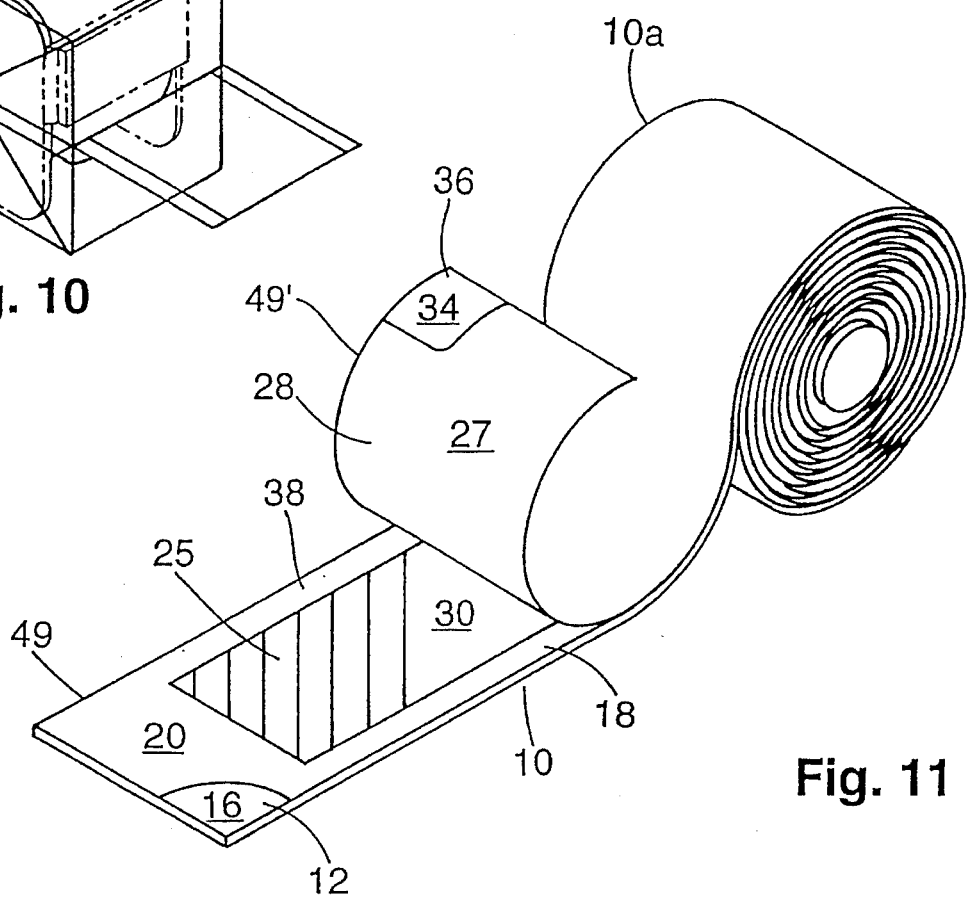
FIG. 11 is a perspective view of the device of FIG. 10 enclosed within a waterproof package.

Referring now to the drawings in detail, there is shown in FIGS. 1 and 11, an unitary device in accordance with the present invention. As shown in FIG. 1, the unitary device, generally designated as 10, includes a padding layer 12 which is preferably made of a material which will not retain water, i.e., non-hydrophilic or substantially hydrophobic, but which allows water to pass through it. The first surface 14 of the padding layer 12, when the device 10 is in use, is placed in contact with the patient's skin. The padding layer 12 is preferably made of a material which is conformable to the patient's skin surface and provides comfort, resiliency and protection. Suitable materials include open-cell polyurethane foam, felt, preferably a felt made of a polyolefin such as polypropylene, and similar materials. By placing a padding layer 12 next to the patient, and not a layer of liquid impermeable and vapor permeable material, such as a polyurethane closed cell foam or other plastic material, patient irritation is minimized as is the potential for increased perspiration moisture and discomfort.

The second surface 16 of the padding layer 12 is juxtaposed against an inner protective layer 18. Preferably, the second surface 16 of the padding layer 12 and the first surface 19 of the inner protective layer 18 are laminated together by heat and pressure. The fabric forming the layer 18 should be flexible. The second, or opposite, surface 20 of the inner protective layer 18, in the assembled device 10 overlays the first surface 22 of the casting layer 24. When cured, the casting layer 24 may have irregular facets or sharp edges. The fabric in the inner protective layer 18 covers these irregularities and prevents damage to the padding layer 12 and the patient's skin. Preferably, the inner protective layer 18 includes a liquid-permeable material which allows liquid, preferably water, to pass through the unitary device 10. The inner protective layer 18 also preferably does not retain water, i.e., the layer 18 is preferably non-hydrophilic or substantially hydrophobic. Preferably, the inner protective layer 18 is a non-woven polypropylene fabric. It should be understood by one of ordinary skill in the art that other suitable fabrics meeting the above criteria may be used without departing from the scope of this invention.

The casting layer 24 includes at least one support substrate 26 such as a woven or knitted fabric. Preferably the substrate 26 is made of a fiberglass warp-knit fabric, wherein the weft or fill yarns of the fabric preferably are made of fiberglass, thermoplastic yarn, natural fiber, thermoplastic/natural fiber blends or combinations thereof. Preferably, the substrate 26 is made of a fiberglass warp and a combination fiberglass and thermoplastic yarn weft. Other suitable fabrics which may be used for the substrate 26 may be found, for example, in U.S. Pat. Nos. 4,667,661 and 4,411,262. Similar fabrics which may be used as a substrate 26 and which can be impregnated with casting resin or plaster of paris are known to those of ordinary skill in the art.

There may be one or more layers of substrate 26 within the unitary device 10. Preferably there are about seven impregnated layers of substrate 26 which together form a composite 25 casting layer 24. Each substrate 26 is preferably impregnated with a resin that when activated by contact with water or other activating liquid will proceed to cure and form the rigid portion of the cast or splint upon final curing. The resin is preferably a water- or other liquid-curable, prepolymer resin useful in the art of casting bandages. Preferably, the resin is water-curable, and is preferably the reaction product of an isocyanate and a propylene glycol. In addition, the resin may be impregnated in or coated upon the substrate 26. Preferably, the resin is impregnated within the substrate 26. Examples of acceptable resins for use in the present device 10, include those disclosed in U.S. Pat. Nos. 4,411,262, 4,502,479 and 4,442,833. While water-curable resins are preferred, other casting compounds, such as plaster of paris, may also be used in the casting layer 24.

As the casting layer 24 requires access to water for activation, it is important that the padding and inner protective layers 12, 18 allow water to pass freely into the layer 20 when the device is wet so that activation can occur. It is also important that the layers in the device 10 not retain excessive water such that the device 10 becomes waterlogged.

A first surface 27 of a first outer protective layer 28 overlays the second surface 30 of the casting layer 24 in juxtaposition. The first outer protective layer 28 preferably includes a liquid-impermeable, water vapor-permeable material such as, for example, a thermoplastic elastomer. More preferably, the first outer protective layer 28 includes a layer of copolyester elastomer in the form of a sheet. An example of such a preferred elastomer is sold commercially as Hytrel®, available from Du Pont. Other similar elastomers and liquid-impermeable, water vapor-permeable materials may be used without departing from the scope of this invention.

The copolyester elastomer chosen, however, preferably delivers a moisture vapor transmission rate of up to about 10,000 g/m$^2$/day. High transmission rates reduce the risk of infection and irritation caused by trapped skin moisture. The high vapor transmission efficiency allows the moisture from perspiration to rapidly evaporate through the device 10 increasing the breathability of the cast or splint. This allows the device 10 to remain on the patient for a longer period of time while minimizing maceration of the skin. The preferred first outer protective layer 28 including copolyester elastomer also provides an increased flexibility enhancing patient comfort and allowing better conformity of the device 10 to the patient. Further, by placing this layer 28 on the outer portion of the device 10, the casting layer 24 is protected against exposure to water once the device is in place on the patient. The liquid impermeable layer 28 blocks liquid from passing through the exterior of the device and accidentally contacting the casting layer 24. However, due to the high moisture vapor transmission rate, moisture trapped in the interior portions of the device 10 quickly and easily dries out.

The second surface 32 of the first outer protective layer 28 is juxtaposed against, and preferably laminated by heat and pressure to, the first surface 34 of a second outer protective layer 36. The second outer protective layer 36 includes a non-hydrophilic (or substantially hydrophobic), liquid-permeable material. Preferably, the second outer protective layer 36 is a non-woven polypropylene fabric similar to the inner protective layer 18, but preferably a lighter weight version of that fabric. The second outer protective layer 36 functions to protect the inner layers, particularly the first outer protective layer 28 of the device 10 from being damaged by an external source. It should be understood by one of ordinary skill in the art that other suitable fabrics meeting the above criteria may be used without departing from the scope of this invention. The layer 36 should also allow free flow of liquid and vapor such that the moisture vapor transmission rate of the first outer protective layer 28 is not impaired.

Once the device 10 is assembled by placing the casting layer 24 between the second surface 20 of the inner protective layer 18 and the first surface 27 of the first outer protective layer 28 as shown in FIG. 2, the overlapping edges 38 of the layers are preferably contacted with a spray adhesive and subjected to heat and pressure to seal the device 10 as shown in FIG. 1. FIG. 2 shows the device 10 of FIG. 1 prior to sealing. Other means for holding the device 10 together may be used, for example, sewing and the like.

The device 10 is preferably made in the form of an elongated, preferably rectangular, configuration as shown in FIG. 2, however, other designs are acceptable. The casting layer 24 should be somewhat smaller in outline than the remaining layers in the device 10 to facilitate peripheral sealing as shown in FIGS. 2 and 11. The casting material should be kept dry until ready for use by sealing the device 10 in a waterproof package 29 as shown in FIG. 10. The device 10 may be sealed in packaging 29 in an elongate form as shown in FIG. 10. Alternatively, if the device 10 is manufactured in individually cut segments, it may be packaged in individual waterproof packages corresponding to the length and width of the cut segments (not shown).

The device 10 may be pre-cut into individually packaged segments or sold in roll form as shown in FIGS. 10 and 11. As the device 10 does not use a sheath or other form-constricting or confining means, the outline and configuration of the individually cut segments may be further cut into particular shapes useful for conforming to typical body areas to be immobilized or supported as shown in FIGS. 4 and 5.

The configuration of the device 40 shown in FIG. 4, for example, is useful for an arm 42. As shown in FIG. 3, the device 40 is applied to an arm 42 forming a splint. The device 40 conforms to the lower portion of the arm 42 and bends upward into the palm of the hand at 44 to form a piece for gripping by the fingers 46. Bandage material (not shown) may be wrapped around the arm and splint to hold the splint in place. The device 48 as shown in FIG. 5, for example, may have a "T" configuration for use as a splint for the hand or wrist. Other configurations may be specifically designed for different body areas, or the device 10 may remain in its preferred manufacturing configuration. If the device 10 is dispensed in roll form, individual pieces of the roll 10a may be cut off and used as needed.

The device 10, in any form, must be sealed in a waterproof container 29, such as metallic foil, plastic or the like. If the device 10 is sold in roll form, the roll 10a should be stored in a waterproof packaging 29. Preferably, the roll 10a is stored on a spool 29' as shown in FIG. 10 prior to sealing in a waterproof container 29. The waterproof container 29 may further be stored in a carton or similar commercial packaging (not shown). In use, when a portion of the device 10 has been cut, the portions of the device 10 remaining on the roll 10a should be resealed in the original package 29.

In one embodiment as shown in FIG. 11, the device 10 includes a first laminated layer 49 including the padding layer 12 and the inner protective layer 18 and a second laminated layer 49' including the first and second outer protective layers 28, 36. The laminated layers 49, 49' are formed prior to assembly of the device 10. The casting layer 26 is placed over the laminated layer 49 such that the first surface 22 of the casting layer 26 is positioned along the second surface 20 of the inner protective layer 18. The second laminated layer 49', more particularly, the first surface 27 of the first outer protective layer 28, is then juxtaposed against the second surface 30 of the casting layer 26. To form the device 10, the laminated and casting layers 49, 49', 26 are held together by means including heat and pressure applied to the overlapping edges 38 as shown in FIG. 2. Preferably, spray adhesive is used on the overlapping edges 38, prior to application of heat and pressure to seal the device 10.

An alternative embodiment of a unitary device, generally designated as 50, and variations of that embodiment are shown in FIGS. 6–9. In FIG. 6, the device 50 may have water or other liquid activating substances added to, or already within, the device 50, i.e., it is not necessary to immerse the device. The inner portion of the device 50 contains a padding layer 52, an inner protective layer 54 and an inner water containment layer 56. The padding layer 52 preferably includes the same materials and serves the same purpose as the padding layer 12 in the device 10 as described above.

The first side 58 of the inner protective layer 54 is juxtaposed against, and preferably laminated by heat and pressure to, the second side 60 of the padding layer 52. Preferably, the inner protective layer 54 includes the same material as the inner protective layer 18 as described above.

The first side 62 of the inner water containment layer 56 is juxtaposed against, and preferably laminated to, the second side 64 of the inner protective layer 54. The inner water containment layer 56 preferably includes a liquid-impermeable and water vapor-permeable material such as the thermoplastic elastomers as described above useful for the first outer protective layer 28 in the form of a sheet. More preferably, the inner water containment layer 56 is formed of a copolyester elastomer such as, for example, Hytrel®. The inner water containment layer 56 may also include other liquid retentive, water vapor permeable materials such as spun-bonded hydrophobic polypropylene non-woven fabric, polyurethane film, a commercial material such as Goretex® and the like.

The outer portion of the device 50 includes the outer water containment layer 66. The device 50 may also include a further, optional, protective layer (not shown) including a non-hydrophilic, water-permeable material in the same manner as the second outer protective layer 36 of the device 10. The outer water containment layer 66 preferably includes a liquid-impermeable and water vapor-permeable material such as the same thermoplastic elastomer used for the inner water containment layer 56 in the form of a sheet. More preferably, the outer water containment layer 66 includes a copolyester elastomer such as, for example, Hytrel®. While the outer water containment layer 66 may also include other liquid retentive, water vapor-permeable materials, in the same manner as the inner water containment layer 56, it is preferred that at least one, and more preferably both, of the water containment layers 56, 66 include a thermoplastic elastomer, preferably a copolyester elastomer such as, for example, Hytrel®.

The inner and outer containment layers 56, 66 are substantially parallel to each other but are spaced apart such that a space 68 is created between the second side 70 of the inner water containment layer 56 and the first side 72 of the outer water containment layer 66. Within the space 68 is positioned a casting member 74. The casting member 74 preferably includes the same material as the casting layer 24 in the device 10. The inner and outer layers 52, 54, 56, 66 of the device 10, are held together by means including heat and pressure. Spray adhesive may also be used to join the inner layers 52, 54, 56, in preferably pre-laminated form, to the outer water containment layer 66. Other means of sealing the device 50 such as sewing, clips and the like may also be used in the same manner as described for device 10. Since the device 50 does not use a sheath or other form-constricting means, the outline and configuration of the device 50 may be of any shape as described above with respect to the device 10.

The outer water containment layer 66 has at least one perforation 76 as shown in FIGS. 7–9 through which a liquid-activating substance, such as water, may be added to the device. Water passes from the second side 78 of the outer water containment layer 66, through the perforation 76 in the layer 66 to the space 68. The liquid may be sealed within the device by plugging the perforation 76 by any suitable means including, but not limited to, a cap, a seal, a clip, a port and the like. Various methods of providing a perforation 76 are shown in FIG. 7 (open end), FIG. 8 (water reservoir) and FIG. 9 (portal).

In FIG. 7, one end of the device 50 is left unsealed to provide an opening 78 into which water may be poured to contact the casting member 74. The entire end may be left open, as shown, or only a portion of one of the ends of the device 50.

In FIG. 8, the perforation 76 includes a water reservoir 80 incorporated within the space 68 of the device 50. The reservoir 80 contains water or other liquid-activating substance and preferably includes a rupturable or puncturable material such as plastic. The reservoir 80 is ruptured by, for example, pressure on the reservoir 80 or punctured by, for example, an external sharp object (not shown). Once open, water or other liquid may enter the space 68 and react with the casting member 74. This variation of the device 50 is completely self-contained and does not require any external water or liquid source for use.

In FIG. 9, the perforation 76 includes a portal 82. The periphery of the device 50 is sealed. The portal 82 is formed in the outer water containment layer 66. Water or other activating liquid may be introduced into the space 68 to react with the casting member 74. The portal 82 may be in the side, edge or on any suitable location on the device 50. The portal 82 may also be in the form of a sealable plug through which a needle may be inserted to inject water, or may be a resealable flap, a removable plug, or any other suitable means by which water or other activating liquid can be introduced into the device 50 and the integrity of the device 50 maintained.

The above variations are for exemplary purposes only and should not be considered limiting. Other similar perforations 76 such as those described above may be made to the self-contained device for either providing a device 50 with its own liquid supply already included in the device 50 or for introducing liquid from an external source into the device 50.

The present invention also includes a method for making a unitary casting device such as the device 10. The method includes impregnating one or more sheets of substrate 26 with a dry casting material, such as a curable resin or plaster of paris as described above, to form a casting layer 24 having a first side 22 and a second side 30. If more than one sheet of substrate 26 is impregnated, the layers of substrate should be stacked to form a composite casting layer 24.

The second side 16 of the padding layer 12 and the first side 19 of the inner protective layer 18 are laminated together, preferably by heat and pressure, to form a first laminate 49. The second side 32 of the first outer protective layer 28 and the first side 34 of the second outer protective layer 36 are also laminated, preferably by heat and pressure, to form a second laminate 49'. The first side 22 of the casting layer 24 is covered with the first laminate 49 such that the first side 22 of the casting layer 24 is juxtaposed against the second side 20 of the inner protective layer. The second side 30 of the casting layer 24 is then covered with the second laminate 49' such that the second side 30 of the casting layer 24 is juxtaposed against the first side 27 of the first outer protective layer 28.

The first laminate 49 and the second laminate 49' are sealed together, preferably by applying a spray adhesive followed by heat and pressure, enclosing the casting layer 24 and forming the unitary device 10.

In the present invention, the devices 10, 50 have an improved vapor permeability in the water-impermeable layers as compared to the vapor permeability of the prior art devices. The construction of the devices 10, 50 of the present invention not only exhibit a better vapor transmission rate, but also contain a better resin barrier such that the applier of the cast is protected from exposure to casting resin. As more harm is incurred by the patient's skin during the wearing of the case from perspiration moisture than from the initial water contact of the skin incurred by immersion of the device 10 for activation or introduction of water into the device 50, the present devices 10, 50 have an improved construction which allows more perspiration to escape away from the skin through the device 10, 50.

The prior art devices by containing a layer of water-impermeable, non-woven polypropylene film next to the patient's skin did cause some instances of skin irritation. The improved construction of the present devices 10, 50 allows for more patient wearing comfort while minimizing skin irritation.

The present preferably non-immersible devices 50 include an improved construction similar to the immersible construction of the device 10 according to the present invention which improves patient comfort, minimizes irritation and improves transmission of vapor through the device 10, 50. The preferably non-immersible devices 50 incorporate an improved, water-impermeable and vapor permeable material for use in forming a liquid-containing pouch in the new construction of the non-immersible design.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A unitary casting device, for making casts and splints, comprising:
   (a) a padding layer for contact with a patient;
   (b) a non-hydrophilic, water-permeable inner protective layer juxtaposed against the padding layer;
   (c) a casting layer placed along the inner protective layer, the casting layer comprising a liquid-activatable casting material;
   (d) a liquid-impermeable, water vapor-permeable first outer protective layer juxtaposed against the casting layer;
   (e) a non-hydrophilic, water-permeable second outer protective layer juxtaposed against the first outer protective layer; and
   (f) means for holding the layers together to form a unitary device.

2. The device according to claim 1, wherein the padding layer comprises a polyolefin felt.

3. The device according to claim 1, wherein the padding layer comprises an open-cell polyurethane foam.

4. The device according to claim 1, wherein the inner protective layer comprises a non-woven polypropylene.

5. The device according to claim 1, wherein the casting layer comprises a fiberglass substrate impregnated with synthetic casting resin.

6. The device according to claim 5, wherein the synthetic casting resin is a water-curable polyurethane prepolymer resin.

7. The device according to claim 1, wherein the casting layer comprises a substrate coated with plaster of paris.

8. The device according to claim 1, wherein the first outer protective layer comprises a thermoplastic elastomer in the form of a sheet.

9. The device according to claim 8, wherein the thermoplastic elastomer is a copolyester elastomer.

10. The device according to claim 1, wherein the second outer protective layer comprises a non-woven polypropylene.

11. The device according to claim 1, wherein the holding means comprises heat and pressure sealing of overlapping edges of the padding, inner protective, first outer protective and second outer protective layers.

12. The device according to claim 11, wherein the holding means further comprises a spray adhesive.

13. A unitary casting device, for making casts and splints, comprising:
   (a) a first laminated layer comprising
      (i) a padding layer for contact with a patient, and
      (ii) a non-hydrophilic, water-permeable inner protective layer;
   (b) a casting layer, placed along the inner protective layer, the casting layer comprising a liquid-activatable casting material;
   (c) a second laminated layer comprising
      (i) a liquid impermeable, water vapor permeable first outer protective layer, and
      (ii) a non-hydrophilic, water-permeable second outer protective layer, wherein the first outer protective layer is juxtaposed against the casting layer; and
   (d) means for holding the laminated and casting layers together to form a unitary device.

14. A unitary casting device, for making casts and splints, comprising:
   (a) a padding layer having a first side and a second side, the first side of the padding layer for contact with a patient;
   (b) a non-hydrophilic, water-permeable inner protective layer having a first side and a second side, the first side of the inner protective layer juxtaposed against the second side of the padding layer;
   (c) an inner water containment layer having a first side and a second side, the first side of the inner water containment layer juxtaposed against the second side of the inner protective layer;
   (d) an outer water containment layer having a first side and a second side, the first side of the water containment layer being substantially parallel to and spaced apart from the second side of the inner water containment layer, forming a space therebetween, the outer water containment layer having at least one perforation through which liquid applied to the second side of the outer water containment layer may pass into the space;
   (e) means for holding the padding, the inner protective, the inner water containment and the outer water containment layers together; and
   (f) a casting member comprising a liquid-activatable casting material positioned within the space.

15. The device according to claim 14, further comprising a non-hydrophilic, water-permeable outer protective layer in contact with the second side of the outer containment layer.

16. The device according to claim 14, wherein at least one of the inner and outer containment layers comprises a thermoplastic elastomer in the form of a sheet.

17. The device according to claim 14, wherein the holding means comprises a spray adhesive.

18. A method for making a unitary casting device, useful for making casts and splints, the method comprising the steps of:

(a) impregnating a sheet of substrate with a dry, liquid-activatable casting material to form a casting layer having a first side and a second side;

(b) laminating a padding layer for contact with a patient to a non-hydrophobic, water-permeable inner protective layer to form a first laminate;

(c) laminating a liquid impermeable, water vapor-permeable first outer protective layer to a non-hydrophilic, water-permeable second outer protective layer to form a second laminate;

(d) covering the first side of the casting layer with the first laminate such that the first side of the casting layer is juxtaposed to the inner protective layer;

(e) covering the second side of the casting layer with the second laminate such that the second side of the casting layer is juxtaposed to the first outer protective layer;

(f) sealing the first and second laminates together such that the casting layer is enclosed thereby forming a unitary device.

19. The method according to claim 18, further comprising the steps of impregnating a plurality of sheets of substrate and layering the sheets to form the casting layer.

20. The method according to claim 18, wherein the first and second laminates are sealed along overlapping edges by means of heat and pressure.

21. The method according to claim 20, wherein the first and second laminates are further sealed along the overlapping edges by means of spray adhesive.

* * * * *